US006426391B1

(12) United States Patent
DeSimone et al.

(10) Patent No.: US 6,426,391 B1
(45) Date of Patent: Jul. 30, 2002

(54) FLUORINATION IN LIQUID OR SUPERCRITICAL CARBON DIOXIDE

(75) Inventors: Joseph M. DeSimone, Chapel Hill, NC (US); Han-Chao Wei, Austin, TX (US); Timothy J. Romack, Durham, NC (US)

(73) Assignees: The University of North Carolina at Chapel Hill, Chapel Hill; North Carolina State University, Raleigh, both of NC (US)

( * ) Notice: Subject to any disclaimer, the term of this patent is extended or adjusted under 35 U.S.C. 154(b) by 0 days.

(21) Appl. No.: 09/307,107

(22) Filed: May 7, 1999

(51) Int. Cl.$^7$ .............................. C08F 8/20; C08F 8/22; C08J 7/12
(52) U.S. Cl. ................. 525/326.4; 525/355; 525/356; 525/357; 525/358; 525/359.1
(58) Field of Search .............................. 525/326.4, 356, 525/355–359.1

(56) References Cited

U.S. PATENT DOCUMENTS

| | | | |
|---|---|---|---|
| 4,994,308 A | 2/1991 | Tarancon | 427/255.1 |
| 5,149,744 A | 9/1992 | Tarancon | 525/356 |
| 5,242,661 A | 9/1993 | Tarancon | 422/131 |
| 5,322,904 A | 6/1994 | Bierschenk et al. | 525/331.6 |
| 5,753,776 A | 5/1998 | Bierschenk | 525/331.6 |

FOREIGN PATENT DOCUMENTS

| | | | | |
|---|---|---|---|---|
| DE | 19833548 A1 | 2/2000 | | C08J/7/12 |
| EP | 0 489 197 A1 | 6/1992 | | C08J/7/12 |

OTHER PUBLICATIONS

International Search Report, PCT/US00/11217, Date of Mailing: Jul. 6, 2000.
R.D. Chambers, *Fluorine in Organic Chemistry*, John Wiley & Sons., pp. 1–13 (1973).
F.A. Cotton et al., *Advanced Organic Chemistry*, 5$^{th}$ Ed., John Wiley & Sons, pp. 544–545 (1988).
M. Hudlicky, *Chemistry of Organic Fluorine Compounds* 2$^{nd}$ Revised Edition, Prentice Hall, pp. 610–614 (1992).
Carstens, N., *New Surface Fluorinated Products*, PRA International Centre for Coatings Technology, Paper 30, pp. 1–16 (1998).
Anand et al., *Surface Fluorination of Polymers*, Organic Chemistry: Principles and Commercial Applications, edited by R.E. Banks et al., Plenum Press, New York, 1994, p. 469–481.
Cauble et al.; *Preparation of Bis(fluoroxy)difluoromethane*, $CF_2(OF)_2$, Journal of the American Chemical Society, 89:8 1962 (Apr. 12, 1967).
Fifolt et al.; *Fluorination of Aromatic Derivatives with Fluoroxytrifluoromethane and Bis(fluoroxy)diffuoromethane*, J. Org. Chem., 50 4576–4582 (1985).
Hudlický; *Chemistry of Organic Fluorine Compounds II A Critical Review*, 1995 American Chemical Society, p. 1011–1147.
Kiplinger et al., *Gas Transport in Partially Fluorinated Low–Density Polyethylenel*, Journal of Applied Polymer Science, 31: 2617–2626 (1986).
Lide, Editor–in–Chief; *CRC Handbook of Chemistry and Physics*, CRC Press, Inc. 78$^{th}$ Edition, 1997–1998.
Rozen; *Selective Fluorinations by Reagents Containing the OF Group*, Chem. Rev. 96 1717–1736 (1996).
Seebach; *Organic Synthesis–Where now?*, Angew. Chem. Int. Ed. Engl. 29 1320–1361 (1990).
Takaoka et al., *F–Propene–Dialkylamine Reaction Products as Fluorinating Agents*, Bulletin of the Chemical Society of Japan, 52:11 3377–3380 (1979).
Volkmann et al.; *Fluorination of Polyethylene Films*, Makromol. Chem., Macromol. Symp. 25 243–248 (1989).
Wilkinson; *Recent Advances in the Selective Formation of the C–F Bond*, Chem. Rev. 92 505–519 (1992).
Zajc et al.; *Thermically–Initiated Fluorinations at Saturated Carbon Atoms with Xenon Difluoride*, Bull. Chem. Soc. Jpn., 59 1659–1661 (1986).

Primary Examiner—D. R. Wilson
(74) Attorney, Agent, or Firm—Myers Bigel Sibley & Sajovec

(57) ABSTRACT

A method of fluorinating a substance comprises providing a reaction mixture comprising a liquid or supercritical carbon dioxide reaction medium, a first reactant, and a second reactant, wherein the first reactant is a fluorinating reagent, and then contacting the first reactant and the second reactant in the carbon dioxide such that the first reactant fluorinates the second reactant.

20 Claims, 1 Drawing Sheet

SEM Photograph (600X) of Fluorinated HDPE

SEM Photograph (600X) of Fluorinated LDPE

FLUORINATION IN LIQUID OR SUPERCRITICAL CARBON DIOXIDE

FIELD OF THE INVENTION

The invention generally relates to processes for fluorinating compounds in carbon dioxide.

BACKGROUND OF THE INVENTION

Fluorination, which is generally defined as the contacting of elemental fluorine, or another fluorinating agent, with a substance, is an important industrial process. The choice of fluorinating agent and fluorination conditions often determine the selectivity of the fluorinaton. The fluorinated substance generally undergoes a temporary or permanent change in its physical or chemical properties. Among the changes typically observed in fluorinated substances are bleaching, purification, enhanced lubricity, enhanced impermeability to certain materials, reduction in flammability, and inertness toward chemical reactions such as, for example, resistance to oxidation. The specific changes that are seen, and their magnitude, often depend upon the fluorination conditions as well as on the nature of the substance that is fluorinated. Fluorination can effect changes in the structure of molecules, for example, by replacing certain atoms or groups of atoms such as hydrogen, chlorine, bromine, iodine, carbonyl groups, and hydroxyl groups with fluorine. Fluorine may also be added to sites of unsaturation such as carbon-carbon double bonds. Fluorinating agents that are often used include, but are not limited to, elemental fluorine, xenon difluoride, and functional amines (e.g., N,N-diethyl-1,1,2,3,3,3-hexafluoropropylamine.

Fluorination is typically carried out in solvents or media that are resistant to reaction with fluorinating agents such as halogen-containing solvents like carbon tetrachloride, chlorofluorocarbons, and fluorocarbons. Notwithstanding any potential advantages, these solvents or media may pose potential health and environmental concerns, and should be controlled to minimize possible exposure of personnel and release to the environment. Such environmental concerns could become problematic since selective fluorination processes are being explored for use in pharmaceutical research.

Thus, there is a need in the art for solvents for fluorination and processes using the same that do not have the shortcomings referred to above.

SUMMARY OF THE INVENTION

The present invention obviates the need for employing organic solvent reaction media in fluorination processes, particularly processes involving pharmaceutcal compounds. In one aspect, the invention provides a method of fluorinating a substance. The method comprises providing a reaction mixture comprising a liquid or supercritical carbon dioxide reaction medium, a first reactant, and a second reactant, wherein the first reactant is a fluorinating agent. The first reactant and the second reactant are then contacted in the carbon dioxide reaction medium such that the first reactant fluorinates the second reactant.

In another aspect, the invention relates to a reaction mixture. The reaction mixture comprises a first reactant comprising fluorine, a second reactant; and a liquid or supercritical carbon dioxide reaction medium, The first reactant and the second reactant are present in the carbon dioxide reaction medium and the first reactant and the second reactant react such that the second reactant becomes fluorinated.

A further discovery is that carbon dioxide may facilitate the fluorination of solid articles, so that fluorination may be faster and penetrate more deeply than is found when fluorine gas is used alone.

These and other aspects and advantages are provided by the present invention.

DETAILED DESCRIPTION OF THE PREFERRED EMBODIMENTS

Figure 1:
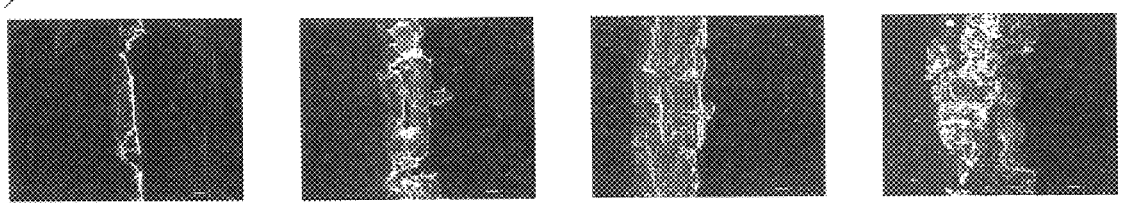
FIG. 1 is an SEM photograph of fluorinated high density polyethylene (HDPE) processed in accordance with a method of the invention.
Figure 2:
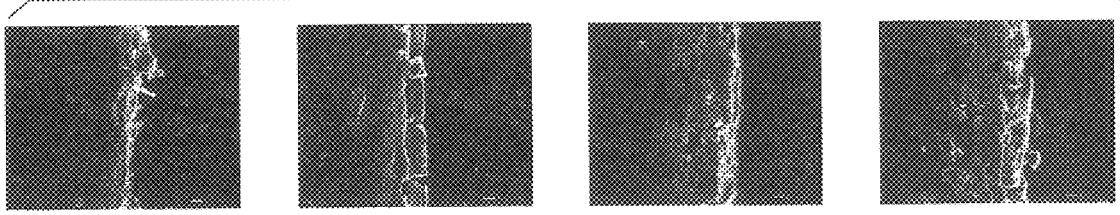
FIG. 2 is an SEM photograph of fluorinated low density polyethylene (LDPE) processed in accordance with a method of the invention.

The present invention now will be described more fully hereinafter with reference to the accompanying specification and examples, in which preferred embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art.

In one aspect, the invention relates to a method of fluorinating a substance. The method comprises providing a reaction mixture comprising a liquid or supercritical carbon dioxide reaction medium, a first reactant, and a second reactant. The first reactant comprises fluorine and, for the purposes of the invention, may be considered a fluorinating agent. The first reactant and the second reactant then come into contact in the carbon dioxide such that said first reactant fluorinates the second reactant. In the invention, neither, either, or both of the first and second reactants being soluble in carbon dioxide.

Although not wishing to be bound by any theory, the second reactant can be thought of as having "reactive sites" that allow for the second reactant to be fluorinated. More specifically, the term "reactive sites" is defined as a location on the second reactant that is capable of reacting with the first reactant (i.e., a fluorinating reagent). Any number of types of reactive sites in accordance with the above definition may be employed for the purposes of the invention. For example, the second reactant may have a reactive site in the form of an unsaturated bond (e.g., a double or triple bond) which may react with the first reactant such that the fluorine becomes attached to the second reactant. As an example, the fluorine may be covalently bonded to the second reactant.

The second reactant may have at least one active group or substituent, For the purposes of the invention, an "active group" is an atom, substituent, or the like, which is known to be capable of being replaced by fluorine in a fluorination reaction by virtue of the reaction between the first reactant and the second reactant. Examples of active groups include, but are not limited to, hydrogen, hydroxyl, carbonyl, and halogens (e.g., chlorine, bromine, or iodine). Examples of second reactants having hydroxyl groups include, but is not limited to, 1-octanol, 2-octanol, and cholesterol.

For the purposes of the invention, carbon dioxide is employed as a fluid in a reaction mixture in a liquid or supercritical phase. The reaction mixture typically employs carbon dioxide as a continuous phase, with the reaction mixture typically comprising from about 50 to about 99.5 percent by weight of carbon dioxide. If liquid $CO_2$ is used, the temperature employed during the process is preferably below 31° C. In one preferred embodiment, the $CO_2$ is utilized in a "supercritical" phase. As used herein, "supercritical" means that a fluid medium is at a temperature that is sufficiently high that it cannot be liquefied by pressure. The thermodynamic properties of $CO_2$ are reported in Hyatt, J. Org. Chem. 49: 5097–5101 (1984); therein, it is stated that the critical temperature of $CO_2$ is about 31° C. In particular, the methods of the present invention may be carded out at a temperature range from about 0° C. to about 110° C. The pressures employed typically range from about 800 psia (5.5 mPa) or to about 5000 psia (3.4 mPa).

As stated hereinabove, the first reactant that is employed in the method of the invention may be characterized as a fluorinating reagent. The term "fluorinating reagent" is defined as a material capable of fluorinating to another compound, such as, for example, a monomer, polymer, or other type of material. Examples of fluorinating agents include, but are not limited to, elemental fluorine, nucleophilic fluorinating agents (e.g., N, N,-diethyl-1,1,2,3,3,3-hexafluoropropylamine), and electrophilic fluorinating agents (e.g., xenon difluorde, hypofluorites). Mixtures of any of the above may be employed. The fluorinating agents that are used are typically soluble in carbon dioxide. The reaction mixture preferably comprises from about 0.5 to about 50 percent by weight of the first reactant or fluorinating agent.

The second reactant that is utilized is one that typically contains at least one reactive site as defined herein. Examples of second reactants include, but are not limited to, organic compounds, organic polymers and inorganic polymers. Included in the above are pharmaceutical compounds. For the purposes of the invention, the term "pharmaceutical compound" is to be broadly construed to cover a wide range of pharmaceutically active compounds. Examples of pharmaceutical compounds include, but are not limited to, sterols (e.g., cholesterol), carbohydrates, amino acids, peptides, nucleosides, antibiotics, anesthetics, mixtures thereof and other materials. Mono- and polyfunctional alcohols may also be employed and include, but are not limited to, cyclohexanol, benzyl alcohol, 1-octanol, 2-octanol, and the like.

Examples of organic polymers that may be fluorinated by the methods of the invention encompass high density polyethylene (HDPE) and low density polyethylene (LDPE). As an example, the polymer may be in the form of an article such as a container, tank, pipe, bottle, plate, rod, or other shape. These articles are sometimes treated with fluorinating agents to fluorinate their surfaces. Fluorination improves chemical resistance, impermeability to hydrocarbons and other liquids and gases, resistance to staining, among other benefits known to those skilled in the art. We have found that fluorination in a reaction medium of carbon dioxide in accordance with this invention can result in a deeper penetration of the fluorinated layer in solid polymer without an increase of contact time, or an equivalent penetration at a shorter reaction time.

The polymers may be fluoropolymers, especially highly fluorinated polymers, that is polymers in which more than 90 percent of the monovalent atoms on the polymer are fluorine. The polymers may be perfluoropolymers. The polymers may be in forms suitable for melt processing. This includes finely divided form such as powder, or it may be pellet or cube form, such as is used in injection molding or extrusion. In general, the polymer may be in the form of a shaped article. The shaped article may be, for example, a vessel having an interior surface which is exposed to said first reactant. It is often necessary to treat fluoropolymers, and especially perfluoropolymers, with fluorine to fluorinate reactive end groups in order to improve the thermal stability of the polymers, particularly thermal stability during melt processing. The reactive end groups come from polymerization initiator radicals, or chain transfer agents that are used in making the polymers. Fluorination of fluoropolymer powders, pellets, and cubes proceeds more rapidly and completely in the carbon dioxide reaction medium in accordance with this invention.

Various additives may be used in the reaction mixtures employed in the methods of the invention if so desired. Examples of these additives include, but are not limited to, additives that regulate molecular weight of the fluorinated products or that control its functionality. Reagents that may control process variables such as reaction times, alter the flow characteristics of the fluid used for the reaction medium may also be employed. Optionally, co-solvents may be used. Mixtures of any of the above components can be employed as known by one skilled in the art.

The methods of the invention may be carried out using known equipment. For example, the fluorination reactions may be carried out either batchwise, continuously, or semi-continuously, in appropriately designed reaction vessels or cells. Additional features may be employed such as, for example, agitation devices (e.g., a paddle stirrer or impeller stirrer) and heaters (e.g., a heating furnace or heating rods).

The following examples are intended to illustrate the invention and are not intended as a limitation thereon. In general, the examples are provided to demonstrate the effectiveness of the methods of the invention. Table 1 is presented and provides a general summary of each example.

TABLE 1

| Example | Substrate | Fluorinating Agent | Condition | Temp (° C.) | Pressure (psia) | $CO_2$ Density | HF Scavenger | Product* |
|---|---|---|---|---|---|---|---|---|
| 1 | Saturated liquid hydrocarbon | Electrophilic | SC $CO_2$ | 105 | 5000 | 0.69275 | None | 30 |
| 2 | Saturated cyclic secondary liquid alcohol | Nucleophilic | Liquid $CO_2$ | 25 | 1000 | 0.73939 | None | 0 |
| 3 | Unsaturated liquid alcohol | Nucleophilic | Liquid $CO_2$ | 25 | 1000 | 0.73939 | None | 60 |
| 4 | Saturated acyclic primary liquid alcohol | Nucleophilic | Liquid $CO_2$ | 25 | 1000 | 0.73939 | None | 68 |
| 5 | Saturated acyclic secondary liquid alcohol | Nucleophilic | Liquid $CO_2$ | 25 | 1000 | 0.73939 | None | 48 |
| 6 | Saturated cyclic secondary solid alcohol | Nucleophilic | Liquid $CO_2$ | 25 | 1000 | 0.73939 | None | 62 |
| 7 | Saturated cyclic secondary solid alcohol | Nucleophilic | Liquid $CO_2$ | 0 | 1000 | 0.95522 | None | 28 |
| 8 | Saturated cyclic secondary solid alcohol | Nucleophilic | Liquid $CO_2$ | 25 | 1000 | 0.73939 | None | 33 |
| 9 | Saturated cyclic secondary solid alcohol | Nucleophilic | Liquid $CO_2$ | 25 | 1000 | 0.73939 | Sodium Fluoride | 37 |
| 10 | Saturated cyclic secondary solid alcohol | Nucleophilic | SC $CO_2$ | 40 | 1200 | 0.31559 | None | 51 |
| 11 | Saturated cyclic secondary solid alcohol | Nucleophilic | SC $CO_2$ | 40 | 1500 | 0.65219 | None | 45 |

TABLE 1-continued

| Example | Substrate | Fluorinating Agent | Condition | Temp (° C.) | Pressure (psia) | $CO_2$ Density | HF Scavenger | Product* |
|---|---|---|---|---|---|---|---|---|
| 12 | Saturated cyclic secondary solid alcohol | Nucleophilic | SC $CO_2$ | 40 | 2000 | 0.76064 | None | 33 |
| 13 | Saturated cyclic secondary solid alcohol | Nucleophilic | SC $CO_2$ | 40 | 3000 | 0.84676 | None | 29 |
| 14 | Saturated cyclic secondary solid alcohol | Nucleophilic | SC $CO_2$ | 40 | 4500 | 0.91596 | None | 26 |
| 15 | Hydrocarbon polymer (HDPE) | Fluorine gas | No $CO_2$ | 21–23 | 16 | — | None | 12–21 |
| 16 | Hydrocarbon polymer (HDPE) | Fluorine gas | Liquid $CO_2$ | 21–23 | 850 | 0.76343 | None | 54–62 |
| 17 | Hydrocarbon polymer (HDPE) | Fluorine gas | SC $CO_2$ | 34–35 | 1150 | 0.49399 | None | 65–75 |
| 18 | Hydrocarbon polymer (HDPE) | Fluorine gas | No $CO_2$ | 34–35 | 16 | — | None | 29–42 |
| 19 | Hydrocarbon polymer (LDPE) | Fluorine gas | No $CO_2$ | 34–35 | 16 | — | None | 12–20 |
| 20 | Hydrocarbon polymer (LDPE) | Fluorine gas | No $CO_2$ | 21–23 | 16 | — | None | 19–20 |
| 21 | Hydrocarbon polymer (LDPE) | Fluorine gas | Liquid $CO_2$ | 21–23 | 850 | 0.76343 | None | 42–58 |
| 22 | Hydrocarbon polymer (LDPE) | Fluorine gas | SC $CO_2$ | 34–35 | 1150 | 0.49399 | None | 42–65 |

EXAMPLE 1

A 25 mL high pressure reactor equipped with a pressure transducer and temperature controller was purged with dry nitrogen for approximately 15 minutes. The reactor was charged with carbon dioxide and 2.0 mL methylcyclohexane and 0.5 g of xenon difluoride. The whole reaction system was closed and the reaction mixture was stirred at 105° C. and at 5000±15 psi (3.4±0.1 MPa) for 3 hours. The resultant solution mixture was analyzed by $^1$H NMR and GC/MS.

EXAMPLE 2

A 25 mL high pressure reactor equipped with a pressure transducer and temperature controller was purged by dry nitrogen for approximately 15 minutes. The reactor was charged with 0.5035 g cyclohexanol. 1.2037 g N,-N-diethyl-1,1,2,3,3,3-hexa-fluoropropylamine was added via a high pressure addition tube under nitrogen atmosphere. The whole reaction system was closed and N,-N-diethyl-1,1,2,3,3,3-hexa-fluoropropylamine was flushed into the 25 mL reactor by using high pressure carbon dioxide. The reaction mixture was stirred at 25° C. and at 1000±15 psi (6.9±0.1 MPa) for 24 hours. The resultant solution mixture was analyzed by $^1$H NMR and GC/MS.

EXAMPLE 3

A 25 mL high pressure reactor equipped with a pressure transducer and temperature controller was purged by dry nitrogen for approximately 15 minutes. The reactor was then charged with 0.6373 g benzyl alcohol. 1.4287 g N,-N-diethyl-1,1,2,3,3,3-hexa-fluoropropylamine was added to a high pressure addition tube under nitrogen atmosphere. The whole reaction system was closed and N,-N-diethyl-1,1,2,3,3,3-hexa-fluoropropylamine was flushed into the 25 mL reactor by using high pressure carbon dioxide. The reaction mixture was stirred at 25° C. and at 1000±15 psi (6.9±0.1 MPa) for 20 hours. The resultant solution mixture was analyzed by $^1$H NMR and GC/MS. The desired fluorinated product, alpha-fluorotoluene, was obtained in 60 percent yield.

EXAMPLE 4

A 25 mL high pressure reactor equipped with a pressure transducer and temperature controller was purged with dry nitrogen for approximately 15 minutes. The reactor was then charged with 0.5721 g 1-octanol. 1.103 g N,-N-diethyl-1,1,2,3,3,3-hexa-fluoropropylamine was added to a high pressure addition tube under nitrogen atmosphere. The whole reaction system was closed and N,-N-diethyl-1,1,2,3,3,3-hexa-fluoropropylamine was flushed into the 25 mL reactor by using high pressure carbon dioxide. The reaction mixture was stirred at 25° C. and at 1000±15 psi (6.9±0.1 MPa) for 20 hours. The resultant solution mixture was analyzed by $^1$H NMR and GC/MS. The desired fluorinated product, 1-fluorooctane, was obtained in 68 percent yield.

EXAMPLE 5

A 25 mL high pressure reactor equipped with a pressure transducer and temperature controller was purged with dry nitrogen for approximately 15 minutes. The reactor was then charged with 0.5745 g 2-octanol. 1.12 g N,-N-diethyl-1,1,2,3,3,3-hexa-fluoropropylamine was added to a high pressure addition tube under nitrogen atmosphere. The whole reaction system was closed and N,-N-diethyl-1,1,2,3,3,3-hexa-fluoropropylamine was flushed into the 25 mL reactor by using high pressure carbon dioxide. The reaction mixture was stirred at 25° C. and at 1000±15 psi (6.9±0.1 MPa) for 20 hours. The resultant solution mixture was analyzed by $^1$H NMR and GC/MS. The desired fluorinated product, 2-fluorooctane, was obtained in 48 percent yield.

EXAMPLE 6

A 25 mL high pressure reactor equipped with a pressure transducer and temperature controller was purged by dry nitrogen for approximately 15 minutes. The reactor was then charged with 0.1585 g cholesterol. 1.2689 g N,-N-diethyl-1,1,2,3,3,3-hexa-fluoropropylamine was added to a high pressure addition tube under nitrogen atmosphere. The whole reaction system was closed and N,-N-diethyl-1,1,2,3,3,3-hexa-fluoropropylamine was flushed into the 25 mL reactor by using high pressure carbon dioxide. The reaction mixtures was stirred at 25° C. and at 1000±15 psi (6.9±0.1 MPa) for 20 hours. The resultant solution mixture was analyzed by $^1$H NMR and GC/MS. The desired fluorinated product, cholesteryl fluoride, was obtained in 62 percent yield.

EXAMPLE 7

A 25 mL high pressure reactor equipped with a pressure transducer and temperature controller was purged with dry nitrogen for approximately 15 minutes. The reactor was then charged with 0.0971 g cholesterol. 1.349 g N,-N-diethyl-1,1,2,3,3,3-hexa-fluoropropylamine was added to a high pressure addition tube under nitrogen atmosphere. The whole reaction system was closed and N,-N-diethyl-1,1,2,3,3,3-hexa-fluoropropylamine was flushed into the 25 mL reactor by using high pressure carbon dioxide. The reaction mixtures were stirred at 0° C. and at 1000±15 psi (6.9±0.1 MPa) for 20 hours. The resultant solution mixture was analyzed by $^1$H NMR and GC/MS. The desired fluorinated product, cholesteryl fluoride, was obtained in 28 percent yield.

EXAMPLE 8

A 25 mL high pressure reactor equipped with a pressure transducer and temperature controller was purged with dry nitrogen for approximately 15 minutes. The reactor was then charged with 0.1033 g cholesterol. 1.2634 g N,-N-diethyl-1,1,2,3,3,3-hexa-fluoropropylamine was added to a high pressure addition tube under nitrogen atmosphere. The whole reaction system was closed and N,-N-diethyl-1,1,2,3,3,3-hexa-fluoropropylamine was flushed into the 25 mL reactor by using high pressure carbon dioxide. The reaction mixture was stirred at 25° C. and at 1000±15 psi (6.9±0.1 MPa) for 20 hours. The resultant solution mixture was analyzed by $^1$H NMR and GC/MS. The desired fluorinated product, cholesteryl fluoride, was obtained in 33 percent yield.

EXAMPLE 9

A 25 mL high pressure reactor equipped with a pressure transducer and temperature controller was purged with dry nitrogen for approximately 15 minutes. The reactor was then charged with 0.1002 g cholesterol and 1.5042 g sodium fluoride. 1.2332 g N,-N-diethyl-1,1,2,3,3,3-hexa-fluoropropylamine was added to a high pressure addition tube under nitrogen atmosphere. The whole reaction system was closed and N,-N-diethyl-1,1,2,3,3,3-hexa-fluoropropyl amine was flushed into the 25 mL reactor by using high pressure carbon dioxide. The reaction mixture was stirred at 25° C. and at 1000±15 psi (6.9±0.1 MPa) for 20 hours. The resultant solution mixture was analyzed by $^1$H NMR and GC/MS. The desired fluorinated product, cholesteryl fluoride, was obtained in 37 percent yield.

EXAMPLE 10

A 25 mL high pressure reactor equipped with a pressure transducer and temperature controller was purged by dry nitrogen for approximately 15 minutes. The reactor was then charged with 0.1018 g cholesterol. 1.1298 g N,-N-diethyl-1,1,2,3,3,3-hexa-fluoropropylamine was added to a high pressure addition tube under nitrogen atmosphere. The whole reaction system was closed and N,-N-diethyl-1,1,2,3,3,3-hexa-fluoropropylamine was flushed into the 25 mL reactor by using high pressure carbon dioxide. The reaction mixture was stirred at 40° C. and at 1200±15 psi (8.3±0.1 MPa) for 20 hours. The resultant solution mixture was analyzed by $^1$H NMR and GC/MS. The desired fluorinated product, cholesteryl fluoride, was obtained in 51 percent yield.

EXAMPLE 11

A 25 mL high pressure reactor equipped with a pressure transducer and temperature controller was purged with dry nitrogen for approximately 15 minutes. The reactor was then charged with 0.1072 g cholesterol. 1.3062 g N,-N-diethyl-1,1,2,3,3,3-hexa-fluoropropylamine was added to a high pressure addition tube under nitrogen atmosphere. The whole reaction system was closed and N,-N-diethyl-1,1,2,3,3,3-hexa-fluoropropylamine was flushed into the 25 mL reactor by using high pressure carbon dioxide. The reaction mixture was stirred at 40° C. and at 1500±15 psi (10.3±0.1 MPa) for 20 hours. The resultant solution mixture was analyzed by $^1$H NMR and GC/MS. The desired fluorinated product, cholesteryl fluoride, was obtained in 45 percent yield.

EXAMPLE 12

A 25 mL high pressure reactor equipped with a pressure transducer and temperature controller was purged with dry nitrogen for approximately 15 minutes. The reactor was then charged with 0.1056 g cholesterol. 1.1132 g N,-N-diethyl-1,1,2,3,3,3-hexa-fluoropropylamine was added to a high pressure addition tube under nitrogen atmosphere. The whole reaction system was closed and N,-N-diethyl-1,1,2,3,3,3-hexa-fluoropropylamine was flushed into the 25 mL reactor by using high pressure carbon dioxide. The reaction mixture was stirred at 40° C. and at 2000±15 psi (13.8±0.1 MPa) for 20 hours. The resultant solution mixture was analyzed by $^1$H NMR and GC/MS. The desired fluorinated product, cholesteryl fluoride, was obtained in 33 percent yield.

EXAMPLE 13

A 25 mL high pressure reactor equipped with a pressure transducer and temperature controller was purged with dry nitrogen for approximately 15 minutes. The reactor was then charged with 0.1054 g cholesterol. 1.2434 g N,-N-diethyl-1,1,2,3,3,3-hexa-fluoropropylamine was added to a high pressure addition tube under nitrogen atmosphere. The whole reaction system was closed and N,-N-diethyl-1,1,2,3,3,3-hexa-fluoropropylamine was flushed into the 25 mL reactor by using high pressure carbon dioxide. The reaction mixture was stirred at 40° C. and at 3000±15 psi (20.6±0.1 MPa) for 20 hours. The resultant solution mixture was analyzed by $^1$H NMR and GC/MS. The desired fluorinated product, cholesteryl fluoride, was obtained in 29 percent yield.

EXAMPLE 14

A 25 mL high pressure reactor equipped with a pressure transducer and temperature controller was purged with dry nitrogen for approximately 15 minutes. The reactor was then charged with 0.1176 g cholesterol. 1.2090 g N,-N-diethyl-1,1,2,3,3,3-hexa-fluoropropylamine was added to a high pressure addition tube under nitrogen atmosphere. The whole reaction system was closed and N,-N-diethyl-1,1,2,3,3,3-hexa-fluoropropylamine was flushed into the 25 mL reactor by using high pressure carbon dioxide. The reaction mixture was stirred at 40° C. and at 4500±15 psi (3.1±0.1 MPa) for 20 hours. The resultant solution mixture was analyzed by $^1$H NMR and GC/MS. The desired fluorinated product, cholesteryl fluoride, was obtained in 26 percent yield.

EXAMPLE 15

202.4 mg of high density polyethylene (HDPE) was placed in a 800 mL reactor and evacuated for at least 3 hours at ambient temperature. Approximately 16 psi (110 kPa) of pure fluorine was slowly introduced into the reactor and the reaction temperature was controlled in the range of 21 to 23° C. The reaction was carried out at about 21–23° C. for 20 hours and then reactor was carefully vented and evacuated under vacuum for at least 4 hours. The fluorinated HDPE was then placed in a vacuum oven for another 20 hours and the weight of fluorinated HDPE was 206.2 mg. The weight increased 3.8 mg. The depth of fluorination of HDPE was 12 to 21 $\mu$m which was measured by scanning electron microscopy.

EXAMPLE 16

200.3 mg of high density polyethylene (HDPE) was placed in a 800 mL reactor and evacuated for at least 3 hours at ambient temperature. Approximately 16 psi (110 kPa) of pure fluorine was slowly introduced into the reactor and the reaction temperature was controlled from 21 to 23+ C. Then, carbon dioxide was slowly added to the reactor until the total pressure of the reaction system was about 850 psi (5.8 MPa). The reaction mixture was stirred at about 21–23° C. for 20 hours and then reactor was carefully vented and evacuated for at least 4 hours. The fluorinated HDPE was then placed in a vacuum oven for another 20 hours and the weight of fluorinated HDPE was 209.3 mg. The weight increased 7.6 mg. The depth of fluorination of HDPE was 54 to 62 $\mu$m which was measured by scanning electron microscopy.

EXAMPLE 17

202.6 mg of high density polyethylene (HDPE) was placed in a 800 mL reactor and evacuated for at least three hours at ambient temperature. Approximately 16 psi (110 kPa) of pure fluorine was slowly introduced into the reactor and the reaction temperature was controlled from 21 to 23° C. Then, carbon dioxide was slowly added to the reactor until the total pressure of reaction system is about 1150 psi (7.9 MPa). The reaction mixture was stirred at about 34–45° C. for 20 hours and then reactor was carefully vented and evacuated for at least 4 hours. The fluorinated HDPE was then placed in a vacuum oven for another 20 hours and the weight of fluorinated HDPE was 213.5 mg. The weight increased 10.9 mg. The depth of fluorination of HDPE was 65 to 75 $\mu$m which was measured by scanning electron microscopy.

EXAMPLE 18

203.0 mg of high density polyethylene (HDPE) was placed in a 800 mL reactor and evacuated for at least three hours at ambient temperature. Approximately 16 psi (110 kPa) of pure fluorine was slowly introduced into the reactor and the reaction temperature was controlled from 21 to 23° C. The reaction was carried out at a temperature from about 34–35° C. for 20 hours and then the reactor was carefully vented and evacuated for at least four hours. The fluorinated HDPE was then placed in a vacuum oven for another 20 hours and the weight of the fluorinated HDPE was determined to be 207.5 mg. The weight increased 4.5 mg. The depth of fluorination of HDPE was 29 to 42 $\mu$m which was measured by scanning electron microscopy.

EXAMPLE 19

192.2 mg of low density polyethylene (LDPE) was placed in a 800 mL reactor and evacuated for at least three hours at ambient temperature. Approximate 16 psi (110 kPa) of pure fluorine was slowly introduced into the reactor and the reaction temperature was controlled between 21 to 23° C. The reaction was carried out between 34 and 35° C. for 20 hours and then reactor was carefully vented and evacuated for at least four hours. The fluorinated LDPE was then placed in a vacuum oven for another 20 hours. The weight of the resulting fluorinated LDPE was determined to be 196.1 mg. The weight increased 3.9 mg. The depth of fluorination of LDPE was 12 to 20 $\mu$m which was measured by scanning electron microscopy.

EXAMPLE 20

195.7 mg of low density polyethylene (LDPE) was placed in a 800 mL reactor and evacuated for at least 3 hours at ambient temperature. Approximately 16 psi (110 kPa) of pure fluorine was slowly introduced into the reactor and the reaction temperature was controlled at 21–23° C. The reaction was carried out from about 20 to 23° C. for 20 hours and then reactor was carefully vented and evacuated for at least four hours. The resulting fluorinated LDPE was then placed in a vacuum for at least four hours. The fluorinated LDPE was then placed in a vacuum oven for another 20 hours and the weight of fluorinated HDPE was determined to be 199.8 mg. The weight increased 4.1 mg. The depth of fluorination of LDPE was 19 to 20 $\mu$m which was measured by scanning electron microscopy.

EXAMPLE 21

195.8 mg of low density polyethylene (LDPE) was placed in a 800 mL reactor and evacuated for at least 3 hours at ambient temperature. Approximate 16 psi (110 kPa) of pure fluorine was slowly introduced into the reactor and the reaction temperature was controlled at 21–23° C. Then, carbon dioxide was slowly added to the reactor until the total pressure of reaction system is about 850 psi (5.8 MPa). Reaction mixture was stirred at about 21–23° C. for 20 hours and then reactor was carefully vented and evacuated for at least 4 hours. The fluorinated LDPE was then placed in a vacuum oven for another 20 hours and the weight of fluorinated LDPE was 203.1 mg. The weight increased 7.3 mg. The depth of fluorination of LDPE was 42 to 58 $\mu$m which was measured by scanning electron microscopy.

EXAMPLE 22

195.0 mg of low density polyethylene (LDPE) was placed in a 800 mL reactor and evacuated for at least three hours at ambient temperature. Approximately 16 psi (110 kPa) of pure fluorine was slowly introduced into the reactor and the reaction temperature was controlled from about 21 to 23° C. Then, carbon dioxide was slowly added to the reactor until the total pressure of reaction system was about 1150 psi (7.9 MPa). The reaction mixture was stirred at about 34 to 45° C. for 20 hours and then reactor was carefully vented and evacuated for at least four hours. The resulting fluorinated LDPE was then placed in a vacuum oven for another 20 hours and the weight of the fluorinated LDPE was 205.5 mg. The weight increased 10.5 mg. The depth of fluorination of HDPE was 42 to 65 $\mu$m which was measured by scanning electron microscopy.

In the drawings, specification, and examples there have been disclosed typical preferred embodiments of the invention and, although specific terms are employed, they are used in a generic and descriptive sense only and not for the purposes of limitation, the scope of the invention being set forth in the following claims.

That which is claimed:

1. A method of fluorinating a substance, said method comprising:

provideing a reaction mixture comprising a liquid or supercritical carbon dioxide reaction medium, a first reactant and an organic polymer, wherein said first reactant is selected from the group consisting of elemental fluorine, N,N-diethyl-1,2,3,3,3-hexafluoropropylamine, xenon difluoride, hypofluorites, and mixtures thereof; and contacting said first reactant and said organic polymer in the carbon dioxide reaction medium such that said first reactant fluorinates said organic polymer.

2. The method according to claim 1, wherein said liquid or supercritical carbon dioxide is present at a pressure ranging from about 800 psia (5.5 MPa) to about 5000 psia (3.4 MPa).

3. The method according to claim 1, wherein said organic polymer is a fluoropolymer suitable for melt processing.

4. The method according to claim 3, wherein said fluoropolymer is a perfluoropolymer.

5. The method according to claim 1, wherein said organic polymer is in the form of a shaped article.

6. The method according to claim 5, wherein said shaped article is a vessel having an interior surface that is exposed to said first reactant.

7. The method according to claim 1, further comprising the step of separating the fluorinated organic polymer from the reaction mixture.

8. The method according to claim 1, wherein said organic polymer has at least one active group, and wherein said step of contacting said first reactant and said organic polymer comprises contacting said first reactant and said organic polymer so that the fluorine present in said first reactant replaces said at least one active group to fluorinate the organic polymer and become covalently bonded to said organic polymer in place of said at least one active group.

9. The method according to claim 8, wherein the at least one active group is selected from the group consisting of hydrogen, hydroxyl, carbonyl, halogen, and mixtures thereof.

10. The method according to claim 1, wherein said organic polymer has at least one unsaturated site, and wherein said step of contacting said first reactant and said organic polymer comprises contacting said first reactant and said organic polymer so that said first reactant reacts with said organic polymer at the unsaturated site such that said organic polymer becomes fluorinated.

11. The method according to claim 10, wherein the at least one unsaturated site is an unsaturated bond, and wherein fluorine from the first reactant becomes covalently bonded to the organic polymer at the at least one unsaturated site.

12. A reaction mixture comprising:

a first reactant;

an organic polymer; and a liquid or supercritical carbon dioxide reaction medium; wherein said first reactant is selected from the group consisting of elemental fluorine, N,N-diethyl-1,1,2,3,3,3-hexafluoro-propylamine, xenon difluoride, hypofluorites, and mixtures thereof, and wherein said first reactant and said organic polymer are present in said carbon dioxide reaction medium, said first reactant and said organic polymer reacting in said carbon dioxide reaction medium such that said organic polymer becomes fluorinated.

13. The mixture according to claim 12, wherein the liquid or supercritical carbon dioxide is present at a pressure ranging from about 800 psia (5.5 MPa) to about 5000 psia (3.4 MPa).

14. The mixture according to claim 12, wherein said organic polymer is a fluoropolymer suitable for melt processing.

15. The mixture according to claim 14, wherein said fluoropolymer is a perfluoropolymer.

16. The mixture according to claim 12, wherein said organic polymer in the form of a shaped article.

17. The mixture according to claim 16, wherein said shaped article is a vessel having an interior surface that is exposed to said first reactant.

18. The mixture according to claim 12, wherein said organic polymer has at least one active group, and wherein said first reactant replaces said at least one active group to fluorinate the organic polymer and become covalently bonded to said organic polymer in place of said at least one active group.

19. The mixture according to claim 18, wherein the at least one active group is selected from the group consisting of hydrogen, hydroxyl, carbonyl, halogen, and mixtures thereof.

20. The mixture according to claim 12, wherein said organic polymer has at least one unsaturated site, and wherein said first reactant reacts with said organic polymer at the unsaturated site such that said organic polymer becomes fluorinated.

* * * * *

UNITED STATES PATENT AND TRADEMARK OFFICE
CERTIFICATE OF CORRECTION

PATENT NO. : 6,426,391 B1
DATED : July 30, 2002
INVENTOR(S) : DeSimone et al.

It is certified that error appears in the above-identified patent and that said Letters Patent is hereby corrected as shown below:

<u>Column 10,</u>
Line 56, please change "N,N-diethyl-1,2,3,3,3" to -- N,N-diethyl-1, 1,2,3,3,3 --.

Signed and Sealed this

Thirty-first Day of December, 2002

JAMES E. ROGAN
*Director of the United States Patent and Trademark Office*